US00RE36648E

United States Patent [19]

Uber, III et al.

[11] E Patent Number: Re. 36,648

[45] Reissued Date of Patent: Apr. 11, 2000

[54] PATIENT INFUSION SYSTEM FOR USE WITH MRI

[75] Inventors: Arthur E. Uber, III, Pittsburgh, Pa.; Seid Waddell, Vermilion, Ohio; John Stulen, Pittsburgh, Pa.; Jon E. Manley, Frederick, Md.; Salvatore J. Dedola, New Kensington, Pa.; Gordon C. Newell, Safety Harbor, Fla.

[73] Assignee: Medrad, Inc., Indianola, Pa.

[21] Appl. No.: 09/027,852

[22] Filed: Feb. 23, 1998

Related U.S. Patent Documents

Reissue of:

[64] Patent No.: 5,494,036
Issued: Feb. 27, 1996
Appl. No.: 08/158,055
Filed: Nov. 26, 1993

[51] Int. Cl.[7] ..... A61B 6/00

[52] U.S. Cl. ..... 600/432; 128/DIG. 1; 604/154; 604/131

[58] Field of Search ..... 600/432, 410, 600/420; 604/65–67, 27, 890.1, 131, 154, 134; 128/DIG. 1, DIG. 12

[56] References Cited

U.S. PATENT DOCUMENTS

| | | |
|---|---|---|
| 3,523,523 | 8/1970 | Reich et al. . |
| 3,812,843 | 5/1974 | Wootten et al. . |
| 3,880,138 | 4/1975 | Wootten et al. . |
| 3,888,239 | 6/1975 | Rubinstein . |
| 4,006,736 | 2/1977 | Kranys et al. . |
| 4,044,757 | 8/1977 | McWhorter et al. . |
| 4,502,488 | 3/1985 | Degironimo et al. . |
| 4,585,009 | 4/1986 | Barker et al. . |
| 4,613,328 | 9/1986 | Boyd ..... 604/156 |
| 4,619,653 | 10/1986 | Fischell . |
| 4,677,980 | 7/1987 | Reilly et al. . |

(List continued on next page.)

FOREIGN PATENT DOCUMENTS

| | | |
|---|---|---|
| 10550A1 | 9/1983 | European Pat. Off. . |
| 518100A1 | 5/1992 | European Pat. Off. . |
| 495287A3 | 6/1992 | European Pat. Off. . |
| 61-155846 | 7/1986 | Japan . |
| 1-1223943 | 9/1989 | Japan . |
| 1-165010 | 11/1989 | Japan . |
| 1-303139 | 12/1989 | Japan . |
| 5-84296 | 4/1993 | Japan . |
| 7-178169 | 7/1995 | Japan . |

OTHER PUBLICATIONS

"Medrad targets market for MRI", Allison Hargraves, Pittsburgh Business Times, V7, n18, p.1(2), Dec. 21, 1987.

"Detection of Acute Avascular Necrosis of the Femoral Head in Dogs: Dynamic Contrast–Enhanced MR Imaging vs Spin–Echo and Stir Sequences", AJR: 159, pp. 1255–1261, Dec. 1992.

"An Infusion Pump that Works in MRI", Anesth Analg 1993: 77: p. 645, Lettersa to the Editor.

"Market Scan", Diagnostic Imaging , Sep. 1988, p. 61.

"InVitro Evaluation of a Mechanical Injector for Infusion of Magnetic Resonance Contrast Media", Investigative Radiology, vol. 26/No. 8, Aug. 1991, pp. 748–751.

*Primary Examiner*—Brian L. Casier
*Attorney, Agent, or Firm*—Gregory L. Bradley

[57] ABSTRACT

This invention relates generally to the field of Magnetic Resonance Imaging (MRI) systems for generating diagnostic images of a patient's internal organs and more particularly, this invention relates to improved MRI systems with decreased interference between the magnetic field used for producing diagnostic images and the magnetic fields generated by the electric motors used for driving the pistons of the contrast media injectors. Additionally, the system employs an improved communication link between an externally located system controller and the injection head control unit located within the electromagnetic isolation barrier which defines the magnetic imaging room.

37 Claims, 2 Drawing Sheets

U.S. PATENT DOCUMENTS

| | | |
|---|---|---|
| 4,695,271 | 9/1987 | Goethel . |
| 4,840,620 | 6/1989 | Kobayashi et al. . |
| 4,854,324 | 8/1989 | Hirschman et al. . |
| 4,981,137 | 1/1991 | Kondo et al. . |
| 5,030,201 | 7/1991 | Palestrant . |
| 5,134,373 | 7/1992 | Tsuruno et al. . |
| 5,236,417 | 8/1993 | Wallis . |
| 5,244,461 | 9/1993 | Derlien . |
| 5,269,762 | 12/1993 | Armbruster et al. . |
| 5,300,031 | 4/1994 | Neer et al. . |
| 5,342,298 | 8/1994 | Michaels et al. . |
| 5,352,979 | 10/1994 | Conturo . |
| 5,354,273 | 10/1994 | Hagen . |
| 5,357,959 | 10/1994 | Fishman . |
| 5,411,485 | 5/1995 | Tennican et al. . |
| 5,417,213 | 5/1995 | Prince . |
| 5,464,014 | 11/1995 | Sugahara ..... 600/411 |
| 5,472,403 | 12/1995 | Cornacchia et al. . |

PATIENT INFUSION SYSTEM FOR USE WITH MRI

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates generally to the field of Magnetic Resonance Imaging (MRI) systems for generating diagnostic images of a patient's internal organs and more particularly, this invention relates to improved MRI systems exhibiting decreased interference between the magnetic field used for producing diagnostic images and spurious magnetic fields created by ancillary equipment, such as the electric motors used for driving the pistons of the contrast media injectors. Additionally, the system employs an improved communication link between an externally located system controller and the injection head control unit which is located within the electromagnetic isolation barrier of the magnetic imaging suite.

2. Description of the Related Art

It has become recognized that MRI systems require isolation from external sources of electromagnetic fields, if optimum image quality is to be obtained from MRI diagnostic procedures. Conventional MRI systems have typically employed some form of electromagnetic isolation chamber which is generally a room enclosed by copper sheeting or conductive mesh material that isolates the room from undesirable sources of electromagnetic radiation and the electromagnetic noise inherent in the atmosphere.

In order to realize the full benefit of the shielded room, these systems employ a controller for the contrast media injector portion of the system which is isolated from the media injector. Such isolation is effected to prevent undesirable electromagnetic radiation generated by the system controller from interfering with the signals used to create the magnetic resonance images.

The external, isolated location of the system controller creates various problems associated with the installation and operation of these systems. One such problem is the need to provide a communications link between the externally located controller and the contrast media injectors, without introducing extraneous electromagnetic radiation. That is, there is a need to provide electrical power supply lines for operation of the contrast media injectors and the injector control circuitry while maintaining the integrity of the electromagnetic shield.

Previous attempts to solve these problems included drilling holes in the wall of the electromagnetic shield for inserting the necessary lines or, alternatively, laying the lines under a shielded floor of the imaging room. These alternatives have proven to be less than optimum, since spurious radiation arose from the presence of the various supply cables within the shielded imaging suite. Additionally, MRI systems which employed these solutions required substantial site dedication and were therefore not very portable.

Another problem associated with conventional magnetic resonance imaging systems is the interference which occurs between the high power magnetic field used for generating the magnetic resonance image and the magnetic fields created by the electric motors which control the operation of the contrast media injection heads. The magnetic field generated by the magnet of the magnetic resonance imaging system is extremely powerful and adversely affects the operation of the electric motors used in the injector head. Additionally, operation of the electric motors in close proximity to the magnetic field used to generate the magnetic resonance image also has an adverse impact on the quality of the resulting image.

In conventional MRI systems, the injection head unit is located adjacent to the patient being examined and the electric motors associated with the injection syringes are directly connected to the syringe pistons. Characteristically, the syringes and the drive motors have been mounted on the injection head unit. The close proximity of the electric motors to the magnetic field used for generating the magnetic resonance image typically resulted in a decrease in motor performance and the ability to control the electric motors used in the injector heads, as well as an overall decrease in system performance.

Accordingly, it is an object of the present invention to provide an improved magnetic resonance imaging contrast media delivery system having decreased interference between the magnetic field used to obtain the magnetic resonance image and the magnetic fields created by ancillary equipment.

It is a further object of this invention to provide an MRI system which minimizes the interference between fields created by the electric motors used to drive the contrast media injection plungers and the magnetic field used to generate the magnetic resonance image.

It is another object of the present invention to provide an MRI contrast media injection system having an improved communication link between the system controller and the injection control unit.

Numerous other objects and advantages of the present invention will be apparent from the following summary, drawings and detailed description of the invention and its preferred embodiment; in which:

SUMMARY OF THE INVENTION

Figure 1:
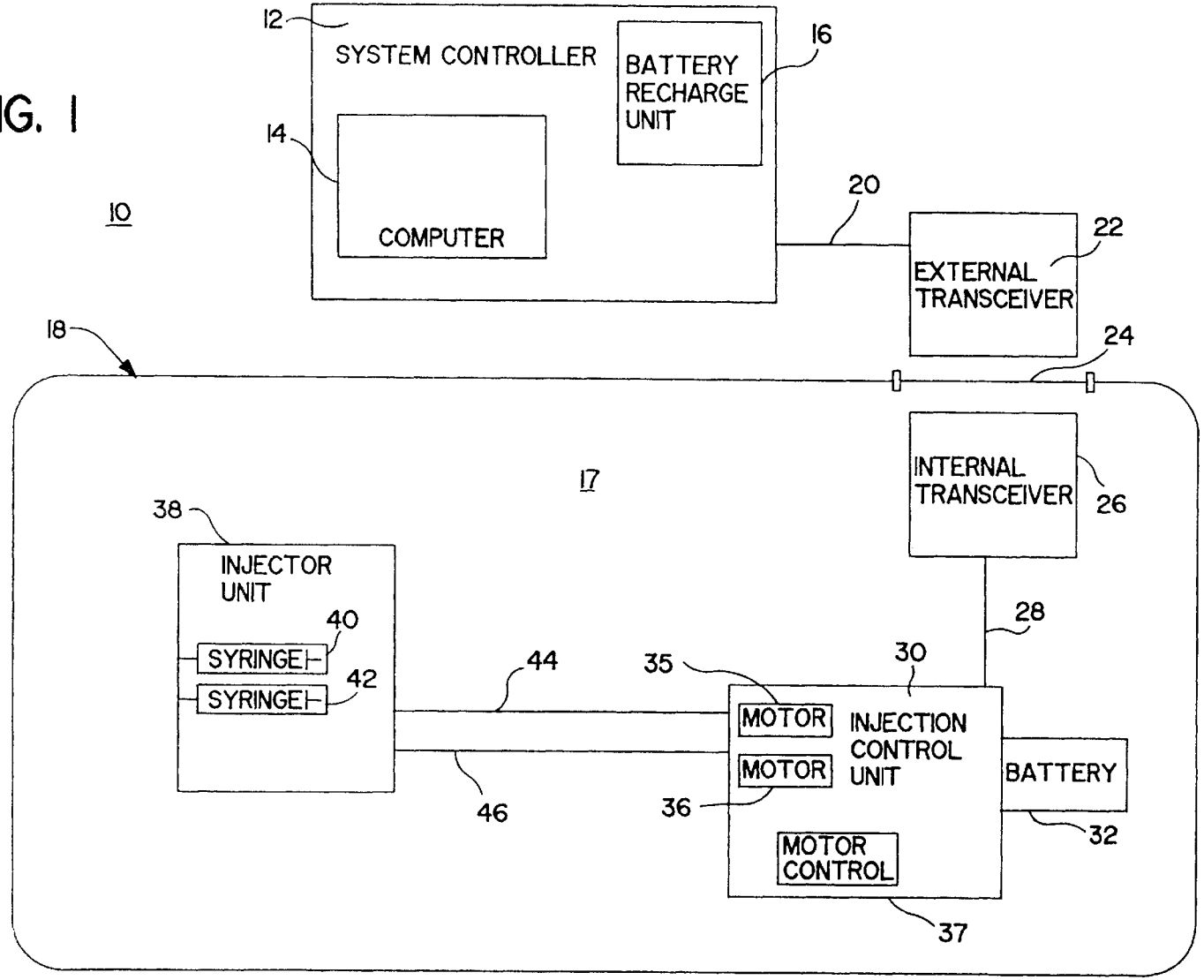
FIG. 1 is a block diagram outlining the functional design of the system; and, FIG. 2 is a diagram illustrating the system of the present invention.
Figure 2:
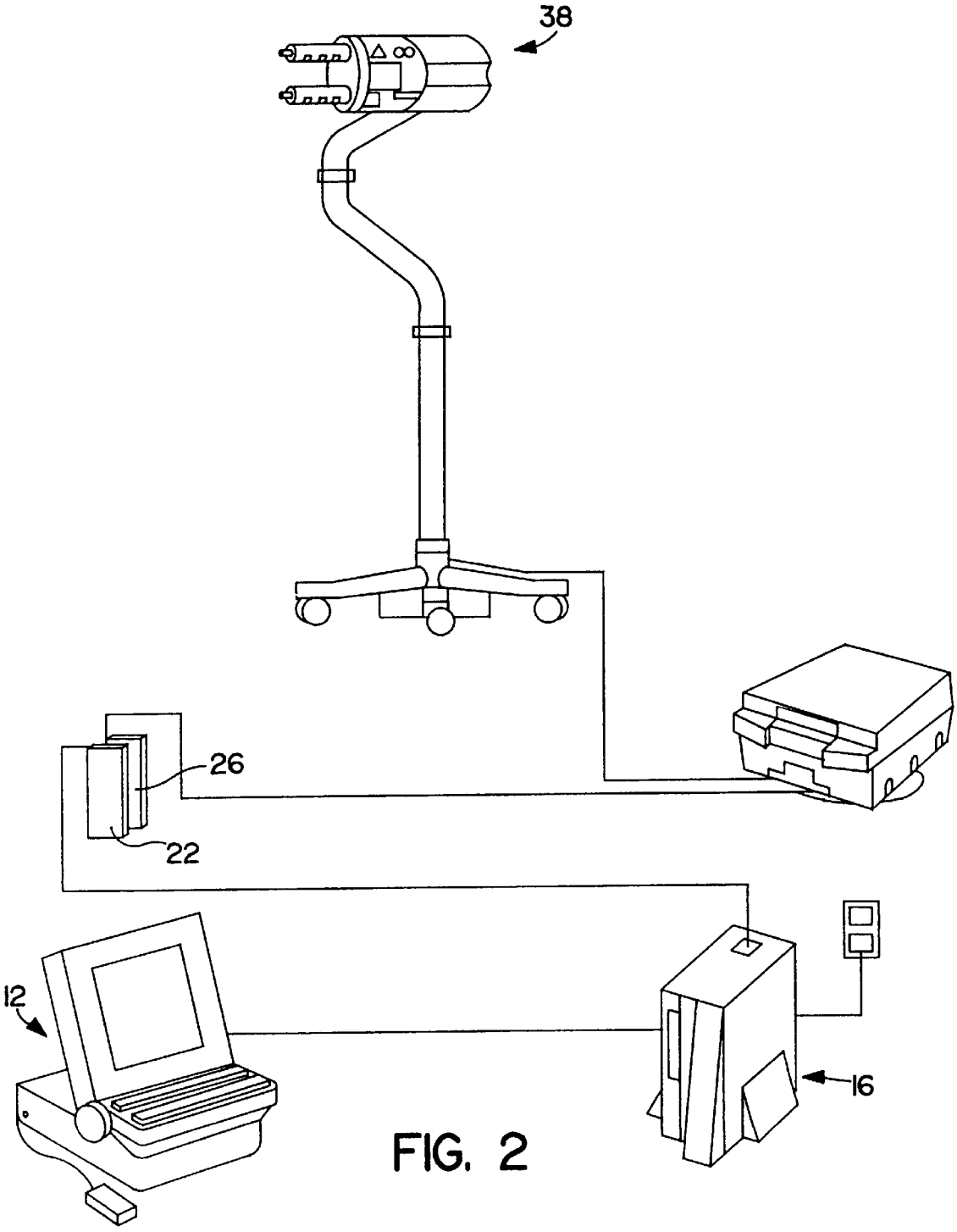

The invention comprises an improved magnetic resonance imaging system which decreases the amount of electromagnetic interference that has heretofore been found within a MRI isolation suite while increasing the portability and ease of system installation. The invention reduces deleterious interaction between the imaging magnetic field and the magnetic field generated by the electric motors which control and operate contrast media injectors.

The system includes a master controller located externally of the shielded imaging room within which a contrast media injection head and a separate injection control unit are located. The system controller communicates with the head control unit via external and internal transceivers which form a communications link for traversing the electromagnetic isolation barrier of the imaging room.

In the preferred embodiment, this communication link is made through a window in the isolation room barrier. These windows are typically in the form of a glass laminate containing a conductive wire mesh, or alternatively, a window that is coated with a thin sheet of conductive material such as gold to maintain the shielding characteristics of the isolation room. The communications link consists of electromagnetic transceivers which operate in a frequency range which permeates the window while maintaining the integrity of the isolation barrier. Infrared or electromagnetic energy in the visual range provide the best results. Alternatively, a fiberoptic communication link can be used to provide the communication link, since fiberoptics do not create electromagnetic radiation.

The present invention also incorporates a contrast media injection unit located within the shielded room which comprises separate contrast media injector head and injection head control unit. The contrast media injection head, and specifically the syringe pistons are located in close proximity to the patient and consequently are located within the powerful magnetic field used to generate the magnetic resonance image. The head control unit which controls operation of the injector head is located from 10–15 feet away from the injector head control unit. The head control unit incorporates electric motors to control and to operate the pistons of syringes used for the injection of patients. A non-rigid operating drive connects the electric motors and control unit to the syringe pistons located on the injection head. In a preferred form, the drive connection can be by way of flexible shafts. Each flexible drive shaft forms a mechanical link between an electric motor located on the head control unit and a piston of the syringes on the injector head. Alternatively, a hydraulic system could be used to control the piston of the injector head. In the preferred embodiment, the flexible drive shaft is manufactured from a non-ferrous metal such as hard brass. The distancing of the head control unit and drive motors from the injector head decreases the adverse effects that the imaging magnetic field has on the electric motors of the injectors and conversely, the adverse affects of spurious electromagnetic radiation arising from operating of the electric motors used to control and operate the contrast media injectors is also reduced significantly.

DETAILED DESCRIPTION OF THE INVENTION

FIG. 1 illustrates an improved magnetic resonance imaging system according to the present invention and is shown generally at 10. The MRI system includes a system controller 12 which incorporates a computer 14 and a battery charging unit 16. The system controller 12 is located externally of the imaging room 17, the imaging room being shielded from electromagnetic interference by a shield 18. Isolation can be achieved by completely enclosing the room with copper sheet material or some other suitable, conductive layer such as wire mesh. Communication line 20, connects the system controller 12 with an external infrared/optical communications transceiver 22. The shielded imaging room 17 also incorporates a patient viewing window 24 in the shield 18 which allows an observer to view the room without breaching the electromagnetic shield 18. The window 24 can be formed by sandwiching a wire mesh material (not shown) between sheets of glass or coating the window with a thin coating of conductive material such as gold (not shown) to maintain the continuity of the electromagnetic shield 18.

An infrared/optical communications transceiver 26 is positioned internally of the imaging room 17 at the viewing window 24 opposite the external communications transceiver 22 such that the internal and external communications transceivers communicate with each other through the viewing window with no breach of the electromagnetic shield. A communications link 28 located within the shielded area connects the internal infrared/optical transceiver with a contrast media injection control unit 30. The injection control unit 30 is powered advantageously by rechargeable battery 32. The injection control unit 30 also incorporates control circuitry which controls electric motors 35, 36 which are also located within the injection control unit. The injection control unit is contained within an electromagnetic shield 37 to prevent the undesired electromagnetic radiation generated by the electric motors from interfering with the magnetic field used to generate the magnetic resonance image.

The injection control unit 30 is separated from the injection head unit 38 by as great a distance as possible. In the preferred embodiment, this is typically ten to fifteen feet. The injection head unit must be located in close proximity to the patient in order to decrease the distance that the contrast media fluid must travel from the contrast media injectors. The injection head unit 38 includes contrast media injection syringe and piston units 40, 42. The syringes 40, 42 are connected to the electric motors in the injection control unit by flexible mechanical drive shafts 44, 46, respectively. The drive shafts are made from a nonferrous metal such as hard brass.

The separation of the electric motors from the injection head, as well as the additional electromagnetic shielding, results in improved system performance and overall resulting image quality. Additionally, the use of an infrared/optical communications link results in a system which is both portable and easy to use.

What we claim is:

[1. A patient infusion control apparatus for use in a magnetic resonance imaging apparatus to generate images of a patient, the patient infusion control apparatus comprising:

a) means for injecting fluid into the patient undergoing a MRI procedure;

b) an electric drive motor and motor control circuitry positioned remotely from the means for injecting to be substantially non-reactive with an electromagnetic field of the imaging apparatus; and, c) a non-rigid drive connection between the electric drive motor and the means for injecting comprising a flexible drive shaft.]

[2. The patient infusion control apparatus of claim 1 wherein the electric drive motor and motor control circuitry are enclosed within electromagnetic shielding.]

[3. The patient infusion control apparatus of claim 1, wherein the patient injection means is adapted to be located in close proximity to the patient.]

[4. The patient infusion control apparatus of claim 1, wherein said flexible drive shaft is comprised of hard brass.]

[5. The patient infusion control apparatus of claim 1, wherein the motor is positioned at least ten to fifteen feet from the patient injection means.]

[6. The patient infusion control apparatus of claim 1, wherein the electric drive motor and the motor control circuitry are enclosed in an electromagnetic shield.]

[7. The patient infusion control apparatus of claim 1, further comprising a rechargeable battery wherein the electric drive motor receives power from the rechargeable battery.]

8. A patient infusion system for use with a magnetic resonance imaging system, the patient infusion system comprising:

a) a room shielded from electromagnetic interference;

b) a system controller located externally of the shielded room;

c) a patient infusion apparatus including infusion apparatus control means for controlling an infusion operation, the patient infusion apparatus located within the shielded room; and, d) a fiber optic communications *control* link between the system controller and the infusion apparatus control means.

9. A patient infusion system for use with a magnetic resonance imaging system, the patient infusion system comprising:

a) a room shielded from electromagnetic interference, which includes a viewing window;

b) a system controller external to the shielded room;

c) a patient infusion apparatus within the shielded room and including infusion apparatus control means for controlling an infusion operation; and, d) a communicating *control* link between the system controller and the infusion apparatus control means, *the control link adapted to be substantially non-reactive with the magnetic field of the imaging system.*

10. The patient infusion system of claim 9, wherein the communications link includes means for transmitting and receiving electromagnetic radiation through the viewing window.

11. The patient infusion system of claim 9, wherein the communications link includes means for transmitting and receiving infrared electromagnetic energy.

12. The patient infusion system of claim 9, wherein the communications link includes means for transmitting and receiving electromagnetic energy in the visual range.

13. A patient infusion system for use with a magnetic resonance imaging system to generate images of a patient, the patient infusion system comprising:

a) a room shielded from electromagnetic interference by an electromagnetic shield including a viewing window;

b) a system controller located outside the room;

c) a patient infusion apparatus located inside the room including infusion apparatus control means for controlling an infusion operation;

d) a communications *control* link between the system controller and the infusion apparatus control means, *the control link adapted to be substantially non-reactive with the magnetic field of the imaging system*; and, e) an electric drive motor and motor control circuitry separated from the patient infusion apparatus and a non-rigid drive connection between the electric drive motor and the patient infusion apparatus [whereby] *wherein* the motor is positioned to be substantially non-reactive with [an electromagnetic] *the magnetic* field of the imaging system.

14. The patient infusion system of claim 13, wherein the communications link comprises an external transceiver located outside the room and an internal transceiver located inside the room, both said transceivers communicating electromagnetic energy through the viewing window in the room.

15. The patient infusion system of claim 14, wherein the electromagnetic energy communicated between said transceivers is in the visible light spectrum.

16. The patient infusion system of claim 14, wherein said electromagnetic energy communicated between said transceivers is in the infrared spectrum.

17. The patient infusion system of claim 13, further comprising a rechargeable battery located in the room and connected to the electric drive motor for providing power to the electric drive motor.

18. The patient infusion system of claim 13, wherein the electric drive motor and motor control circuitry are enclosed within the electromagnetic shield.

19. The patient infusion system of claim 13, wherein the infusion apparatus control means is adapted to be located at least ten to fifteen feet from the patient.

20. The patient infusion system of claim 13, wherein the non-rigid drive connection is comprised of hard brass.

21. The patient infusion system of claim 13, wherein the patient infusion apparatus is adapted to be located in close proximity to the patient.

22. [A method of patient infusion for use with a magnetic resonance imaging system, the method comprising the steps of:

a) providing patient infusion apparatus having a patient infusion apparatus controller and means operable to inject fluid into a patient;

b) positioning the patient infusion apparatus controller away from the patient infusion apparatus to prevent interference in the image, the infusion apparatus controller including at least one electric motor and motor control circuitry; and c) operably connecting the electric motor for controlling the patient infusion apparatus to the patient infusion apparatus with a non-rigid drive connection, the electric motor operating the patient infusion apparatus to infuse media into a patient.] *The patient infusion system of claim 9 wherein the communications link comprises a fiber optic line.*

23. A method of patient infusion for use with a magnetic resonance imaging system, the method comprising the steps of:

a) providing a room shielded from electromagnetic interference including a viewing window;

b) providing a system controller located outside the room;

c) providing a patient infusion apparatus including infusion apparatus control means for controlling an infusion operation, the patient infusion apparatus located inside the room; and d) transmitting control signals from the system controller to the infusion apparatus control means through the viewing window.

*24. The method of claim 23 wherein the control signals are transmitted via electromagnetic transceivers.*

*25. A patient infusion system for use with a magnetic resonance imaging system, the patient infusion system comprising:*

*an infusion apparatus positioned within a room shielded from electromagnetic interference, the infusion apparatus comprising an injector adapted to accommodate at least two syringes mounted thereon for injecting fluid into a patient during a magnetic resonance imaging procedure, the at least two syringes operably engaged with at least one drive mechanism of the injector; and*

*a system controller positioned external to the shielded room and in communication with the infusion apparatus for controlling the operation thereof.*

*26. The patient infusion system of claim 25 wherein the infusion apparatus further comprises an injector control unit positioned within the shielded room.*

*27. The patient infusion system of claim 26 wherein the injector control unit comprises a battery for powering the injector.*

*28. The patient infusion system of claim 26 wherein the injector control unit is remotely positioned from the injector.*

*29. The patient infusion system of claim 28 wherein the injector and the injector control unit are connected by a non-rigid drive connection.*

*30. The patient infusion system of claim 25 wherein the infusion apparatus and the system controller communicate with each other by means of a communication link disposed therebetween.*

*31. The patient infusion system of claim 30 wherein the communication link comprises a fiber optic line.*

*32. The patient infusion system of claim 30 wherein the communication link comprises means for transmitting and receiving electromagnetic radiation through a window in the shielded room.*

*33. A patient infusion system for use with a magnetic resonance imaging system, the patient infusion system comprising:*

*an infusion apparatus positioned within a room shielded from electromagnetic interference, the infusion apparatus comprising an injector for injecting fluid into a patient during a magnetic resonance imaging procedure;*

*a system controller positioned external to the shielded room; and*

*a communication control link between the infusion apparatus and the system controller for controlling the operation of the infusion system, the control link adapted to be substantially non-reactive with the magnetic field of the imaging system.*

*34. The patient infusion system of claim 33, further comprising at least one battery for powering the infusion apparatus.*

*35. The patient infusion system of claim 34 wherein the system controller comprises a battery charger for recharging the at least one battery.*

*36. The patient infusion system of claim 33 wherein the injector is adapted to accommodate at least two syringes mounted thereon.*

*37. A method of infusing a patient with fluid during a magnetic resonance imaging procedure, the method comprising the following steps:*

*providing an injector adapted to accommodate at least two syringes mounted thereon for injecting fluid into a patient during a magnetic resonance imaging procedure, the at least two syringes operably engaged with at least one drive mechanism of the injector, the injector positioned adjacent to the patient within a room shielded from electromagnetic interference;*

*injecting fluid contained within the at least two syringes into the patient; and*

*generating magnetic resonance images of the patient.*

*38. A method of patient infusion for use with a magnetic resonance imaging system, the method comprising the following steps:*

*providing a room shielded from electromagnetic interference;*

*providing a system controller positioned external to the shielded room;*

*providing an infusion apparatus positioned within the shielded room; and*

*transmitting control signals via a communication link between the system controller and the infusion apparatus, the control signals adapted to be substantially non-reactive with the magnetic field of the imaging system.*

*39. The method of claim 38 wherein the communication link comprises a fiber optic line.*

*40. The method of claim 38 wherein the communication link comprises electromagnetic transceivers that transmit the control signals through a window in the shielded room.*

*41. A patient infusion system for use with a magnetic resonance imaging system, the patient infusion system comprising:*

*a patient infusion apparatus within a room shielded from electromagnetic interference including a viewing window;*

*a system controller external to the shielded room; and*

*a communicating control link between the system controller and the infusion apparatus, the control link comprising means for transmitting and receiving electromagnetic energy through the viewing window.*

*42. The system of claim 41 wherein the electromagnetic energy is in the visible light spectrum.*

*43. The system of claim 41 wherein the electromagnetic energy is in the infrared spectrum.*

*44. The system of claim 41 wherein the electromagnetic energy comprises electromagnetic radiation.*

* * * * *